United States Patent
Bulte et al.

(10) Patent No.: US 11,452,507 B2
(45) Date of Patent: Sep. 27, 2022

(54) METHOD AND SYSTEM FOR MONITORING ULTRASOUND PROBE HEALTH

(71) Applicant: GE Precision Healthcare LLC, Wauwatosa, WI (US)

(72) Inventors: Jean Bulte, Peymeinade (FR); Jean-Francois Gelly, Mougins (FR); Geir Ultveit Haugen, Stabekk (NO); Bruno H. Haider, Rehoboth Beach, DE (US); Gilles Thouret, Valbonne (FR); Julia Labrune, Antibes (FR); Delphine Cotta, Vallauris (FR); Ryan Rindler, Denver, CO (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 144 days.

(21) Appl. No.: 17/007,256

(22) Filed: Aug. 31, 2020

(65) Prior Publication Data

US 2022/0065822 A1    Mar. 3, 2022

(51) Int. Cl.
*A61B 8/00*     (2006.01)
*G01N 29/30*   (2006.01)
(Continued)

(52) U.S. Cl.
CPC ............ *A61B 8/58* (2013.01); *G01N 29/24* (2013.01); *G01N 29/30* (2013.01); *G01N 29/44* (2013.01); *G01N 2291/106* (2013.01)

(58) Field of Classification Search
CPC .......... A61B 8/58; G01N 29/24; G01N 29/30; G01N 29/44; G01N 2291/106; G01S 7/5205; G01S 7/52052
(Continued)

(56) References Cited

U.S. PATENT DOCUMENTS 7,415,371 B2   8/2008   Sabourin et al.
7,481,577 B2   1/2009   Ramamurthy et al.
(Continued)

FOREIGN PATENT DOCUMENTS

WO   WO-2019140134 A1 *   7/2019   ............... A61B 8/06

OTHER PUBLICATIONS

FDA, "Marketing Clearance of Diagnostic Ultrasound Systems and Transducers", Guidance for Industry and Food and Drug Administration Staff, U.S. Food & Drug Administration, Jun. 27, 2019, 64 pages.

*Primary Examiner* — Lisa M Caputo
*Assistant Examiner* — Rose M Miller
(74) *Attorney, Agent, or Firm* — McAndrews, Held & Malloy, Ltd.; Jacob Groethe; David Bates

(57) ABSTRACT

A system and method for monitoring ultrasound probe health is provided. The method includes acquiring test data from a plurality of elements of an ultrasound probe by, for each of the plurality of elements, transmitting an ultrasonic signal from one of the elements and receiving a signal on two or more of the elements based on the transmitted ultrasonic signal. The method includes automatically analyzing the test data from the elements to determine a health report for the ultrasound probe. The health report includes a health status for each of a plurality of components of the ultrasound probe. At least one of the components is not part of a transducer array. The method includes automatically displaying the health report on a display device. The health report includes information for at least one of the components.

25 Claims, 6 Drawing Sheets

(51) Int. Cl.
  *G01N 29/44* (2006.01)
  *G01N 29/24* (2006.01)
(58) Field of Classification Search
  USPC .......................................................... 703/103
  See application file for complete search history.

(56) References Cited

U.S. PATENT DOCUMENTS

| | | |
|---|---|---|
| 8,792,295 B2 | 7/2014 | Kristoffersen et al. |
| RE46,603 E | 11/2017 | Kristoffersen et al. |
| 10,024,956 B2 | 7/2018 | Thattari Kandiyil et al. |
| 10,509,014 B2 | 12/2019 | Segall |
| 2020/0245978 A1* | 8/2020 | Shidara ................ A61B 8/5207 |
| 2020/0329324 A1* | 10/2020 | Loeppert .................. H04R 3/04 |
| 2021/0328564 A1* | 10/2021 | Chen ....................... G01N 29/44 |

* cited by examiner

METHOD AND SYSTEM FOR MONITORING ULTRASOUND PROBE HEALTH

FIELD

Certain embodiments relate to ultrasound imaging. More specifically, certain embodiments relate to a method and system for monitoring ultrasound probe health for an ultrasound probe having a transducer array having a plurality of elements.

BACKGROUND

Ultrasound imaging is a medical imaging technique for imaging organs and soft tissues in a human body and an imaging technique for non-destructive testing of materials. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a valuable, non-invasive tool for diagnosing various medical conditions. Ultrasound probes are typically maintained by manually performing a probe maintenance test when an ultrasound operator notices a serious defect with the ultrasound probe. To perform maintenance on an ultrasound probe, a maintenance mode is entered and a protocol for testing the ultrasound probe is performed manually. The protocol for testing an ultrasound probe may be a time consuming process and may require the skill and experience of a field engineer. Moreover, existing probe maintenance protocols are unable to analyze probe components individually, making the probe evaluation and diagnosis tedious and complicated. Furthermore, existing ultrasound probe monitoring systems do not evaluate an impact of the probe defects on image quality.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for monitoring ultrasound probe health, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
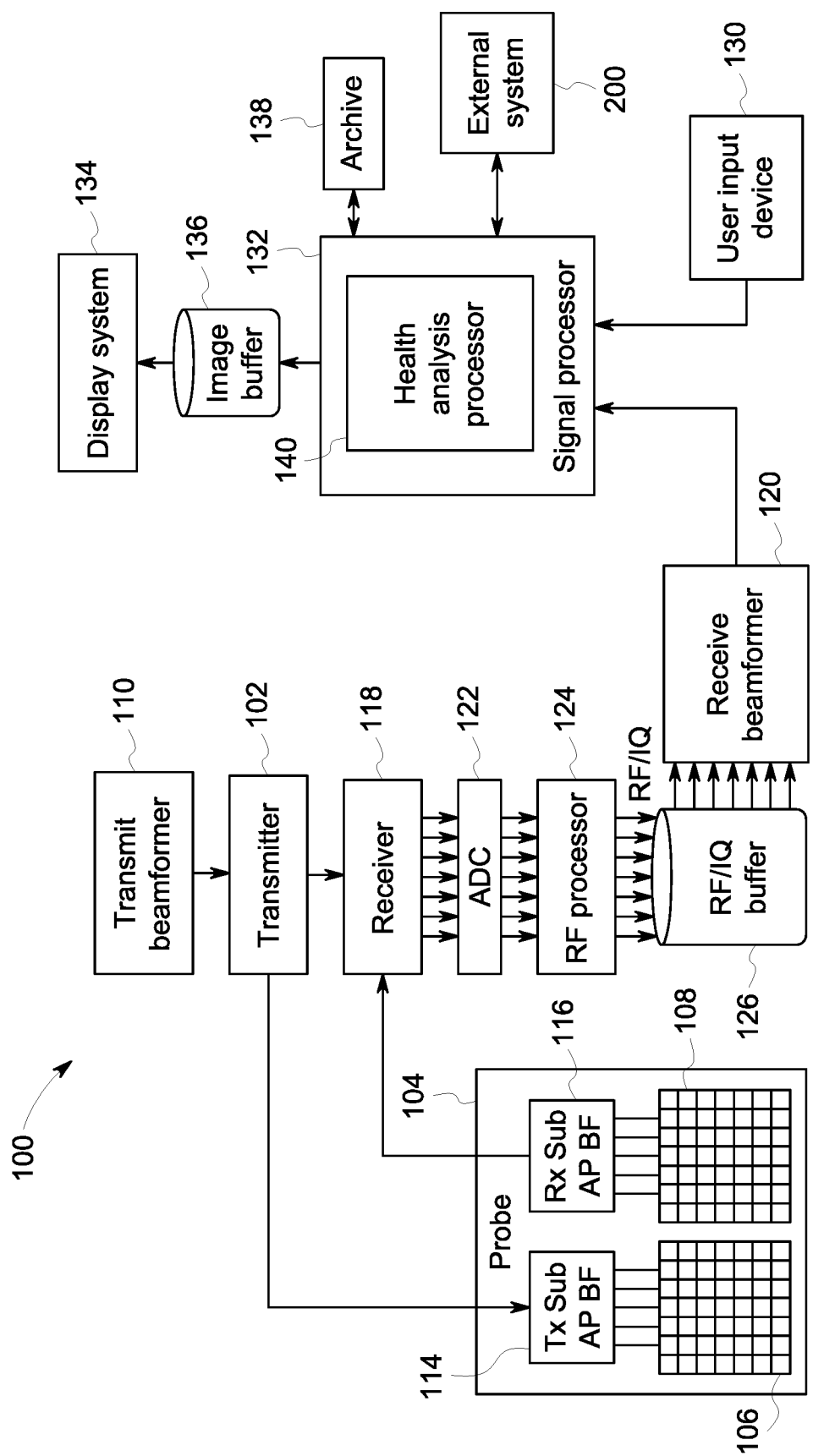
FIG. 1 is a block diagram of an exemplary ultrasound system communicatively coupled to an external system, the ultrasound system and/or the external system operable to monitor ultrasound probe health, in accordance with various embodiments.

Certain embodiments may be found in a method and system for monitoring ultrasound probe health for an ultrasound probe having a transducer array having a plurality of elements. Various embodiments have the technical effect of automatically analyzing ultrasound probe health in scan mode each time the ultrasound probe is connected or used. Certain embodiments have the technical effect of analyzing probe components, such as the transducer elements, lens, oil, cap, electrical circuits, potential multiplexer, and the like, individually. Various embodiments have the technical effect of analyzing image quality metrics, such as resolution, sensitivity, contrast, and the like, to evaluate an impact of probe defects on image quality.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a single-purpose or general-purpose processing unit or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising," "including," or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode (2D mode), M-mode, three-dimensional (3D) mode, CF-mode, PW Doppler, CW Doppler, MGD, and/or sub-modes of B-mode and/or CF such as Shear Wave Elasticity Imaging (SWEI), TVI, Angio, B-flow, BMI, BMI_Angio, and in some cases also MM, CM, TVD where the "image" and/or "plane" includes a single beam or multiple beams.

Furthermore, the term processor or processing unit, as used herein, refers to any type of processing unit that can carry out the required calculations needed for the various embodiments, such as single or multi-core: CPU, Accelerated Processing Unit (APU), Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 communicatively coupled to an external system 200, the ultrasound system 100 and/or the external system 200 operable to monitor ultrasound probe health, in accordance with various embodiments. Referring to FIG. 1, there is shown an ultrasound system 100 communicatively coupled to an external system 200. The ultrasound system 100 comprises a transmitter 102, an ultrasound probe 104, a transmit beamformer 110, a receiver 118, a receive beamformer 120, A/D converters 122, a RF processor 124, a RF/IQ buffer 126, a user input device 130, a signal processor 132, an image buffer 136, a display system 134, and an archive 138.

The transmitter 102 may comprise suitable logic, circuitry, interfaces and/or code that may be operable to drive an ultrasound probe 104. The ultrasound probe 104 may comprise a two dimensional (2D) array of piezoelectric, capacitive micro-machined ultrasonic transducer (CMUT), micro-machined ultrasonic transducers (MUT) elements, or the like. The ultrasound probe 104 may comprise a group of transmit transducer elements 106 and a group of receive transducer elements 108, that normally constitute the same elements. The ultrasound probe 104 may comprise a housing, cap, lens, a matching layer, a backing structure, a flex, a wire, an application-specific integrated circuit (ASIC), and/or an amount of oil, among other things. In certain embodiment, the ultrasound probe 104 may be operable to acquire ultrasound image data covering at least a substantial portion of an anatomy, such as the heart, a blood vessel, a fetus, or any suitable anatomical structure. For example, a transducer array of piezoelectric elements 106 may each generate ultrasound signals (e.g., acoustic waves) that are directed toward a target, such as the region of interest (ROI). At least a portion of the ultrasound signals are reflected off the target back toward the transducer elements 108 as echoes. The transducer elements 106, 108 may include a housing that provides structural support for the transducer elements 106, 108. For example, the housing may be an enclosure that forms a body of the ultrasound probe 104. The transducer elements 106, 108 may include an acoustic stack comprising a piezoelectric layer coupled to a ground electrode and a signal electrode. The electrodes may be provided as layers that extend over all or substantially all of the footprint of the piezoelectric layer, or may be provided as another shape and/or extend over less than all of the footprint of the piezoelectric layer. The electrodes may be conductively coupled to the ASIC by one or more busses, flexes, wires, cables, and the like. The acoustic stack may also include one or more matching layers disposed on the piezoelectric layer and a backing layer assembly disposed below the piezoelectric layer. A cap and/or lens may provide a cover of the ultrasound probe 104. In various embodiments, oil may be present between the acoustic stack and the ultrasound cap and/or lens.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beamformer, which may be digital. In various embodiments, the ultrasound system 100 comprises a plurality of receive beamformers 120.

The user input device 130 may be utilized to input patient data, scan parameters, settings, select protocols and/or templates, select an examination type, and the like. In an exemplary embodiment, the user input device 130 may be operable to configure, manage and/or control operation of one or more components and/or modules in the ultrasound system 100. In this regard, the user input device 130 may be operable to configure, manage and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder (s), a touchscreen, a touch pad, a trackball, motion tracking, voice recognition, a mousing device, keyboard, camera and/or any other device capable of receiving a user directive. In certain embodiments, one or more of the user input devices 130 may be integrated into other components, such as the display system 134, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), an enterprise archive (EA), a vendor-neutral archive (VNA), or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise a health analysis processor 140. The signal processor 132 may be capable of receiving input information from a user input device 130 and/or archive 138, receiving image data, generating an output displayable by a display system 134, and manipulating the output in response to input information from a user input device 130, among other things. The signal processor 132, including the health analysis processor 140, may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 5-120 frames per second but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include a health analysis processor 140 that comprises suitable logic, circuitry, interfaces and/or code that may be operable to automatically analyze test data from a plurality of elements of an ultrasound probe 104 to determine a health report for the ultrasound probe. The test data may be acquired by the ultrasound probe 104 transmitting an ultrasonic signal from one of the transducer elements 106 of a transducer array of the ultrasound probe 104 and receiving a signal on at least two of the transducer elements 108 in response to the transmitted ultrasonic signal. Accordingly, the ultrasonic signal is transmitted from a small aperture and the received signal is received on a receive aperture that is larger than the transmit aperture. The procedure continues by shifting the position of the transmit aperture by transmitting an ultrasonic signal from another of the transducer elements 106 until performance characteristics of each individual component of the ultrasound probe 104, such as the cap, lens, matching layer(s), piezoelectric element(s), CMUT element(s), MUT element(s), backing structure, flex, wire, ASIC, and/or oil can be determined.

Figure 2:
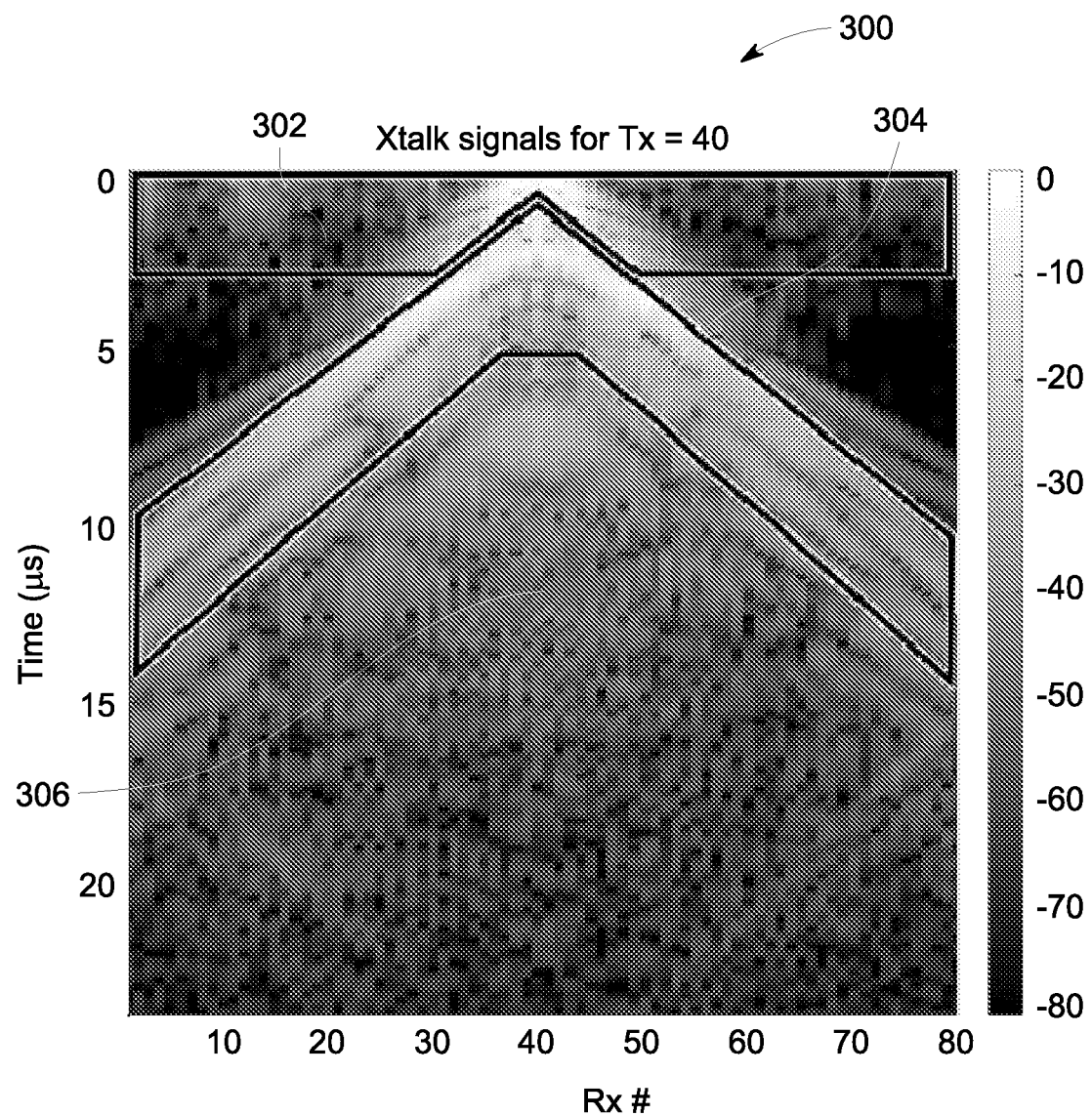
FIG. 2 is an exemplary display of a representation of a cross-talk acquisition sequence, in accordance with various embodiments.

The health analysis processor 140 comprises suitable logic, circuitry, interfaces and/or code that may be operable to analyze the test data. For example, the health analysis processor 140 may be configured to perform a cross-talk acquisition sequence where one element (or a group of elements) is fired and all of the elements record ultrasound signals as receive elements. The process is repeated for all elements (or groups of elements) as transmit elements. FIG. 2 is an exemplary display 300 of a representation of a cross-talk acquisition sequence, in accordance with various embodiments. Referring to FIG. 2, the display 300 illustrates a representation of a cross-talk acquisition sequence having three distinct zones including a cross-talk zone 302, a lens echoes zone 304, and a back-scattering zone 306. The representation of the cross-talk acquisition sequence is not typically displayed. Instead, the raw data of the cross-talk acquisition sequence may be analyzed and stored at archive 138 or any suitable data storage medium. The health analysis processor 140 may be configured to analyze the zones of the cross-talk acquisition sequence to generate a health report for the ultrasound probe 104. For example, the health analysis processor 140 may analyze test data in the cross-talk zone 302 to identify issues with electrical circuits and/or the stack structure of the ultrasound probe 104. As another example, the health analysis processor 140 may analyze test data in the lens echoes zone 304 to identify issues with the lens, transmit transducer elements 106, and/or receive transducer elements 108. The health analysis processor 140 may analyze test data in the back-scattering zone 306, for example, to identify issues with the transmit transducer elements 106 and/or receive transducer elements 108.

Figure 3:
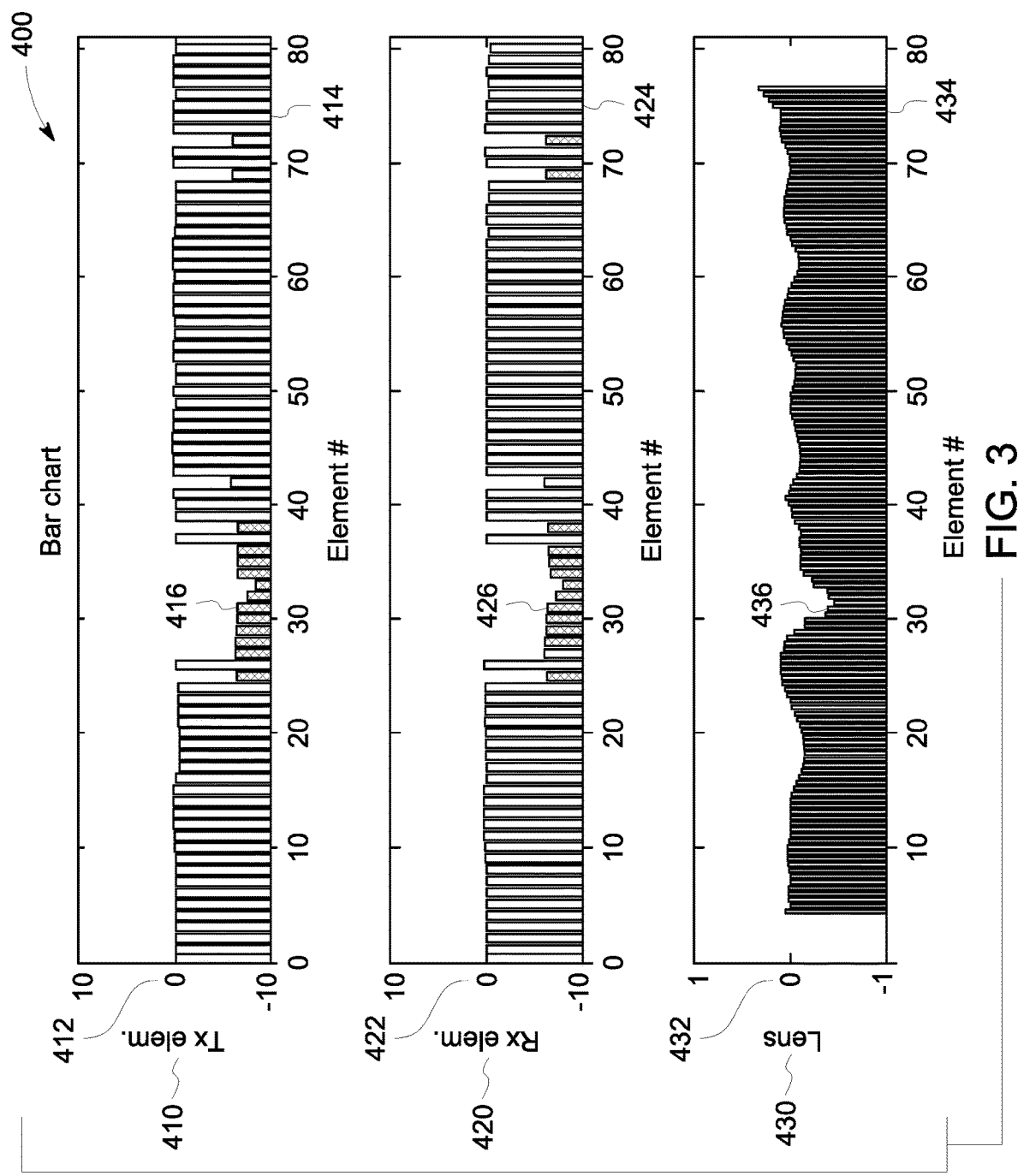
FIG. 3 is an exemplary display of a health report providing an individual score for each of a plurality of ultrasound probe components, in accordance with various embodiments.

Referring again to FIG. 1, the health analysis processor 140 comprises suitable logic, circuitry, interfaces and/or code that may be operable to generate a health report based on the analyzed test data from the plurality of elements of the ultrasound probe 104. The health report may provide an individual score, generated by the health analysis processor 140, for each of the ultrasound probe components, such as the cap, lens, matching layer(s), piezoelectric element(s), CMUT element(s), MUT element(s), backing structure, flex, wire, ASIC, and/or oil. FIG. 3 is an exemplary display 400 of a health report providing an individual score 416, 426, 436 for each of a plurality of ultrasound probe components 414, 424, 434, in accordance with various embodiments. Referring to FIG. 3, the display 400 presents a health report of transmit transducer elements 410, 414, receive transducer elements 420, 424, and lens areas 430, 434. Each of the transmit transducer 410, receive transducer 420, and lens 430 of the health report provide an individual score 416, 426, 436 corresponding to each element 414, 424, 434. The individual scores 416, 426, 436 may be in reference to a baseline 412, 422, 432. The baseline 412, 422, 432 may be tuned for the specific component 410, 420, 430 representing a peak and/or an acceptable operating condition. The health report is represented as bar charts in FIG. 3; however, lists, graphs, numerical scores, or any suitable visual identifier of the component 410, 420, 430 and element 414, 424, 434 scores 416, 426, 436 may be provided. In various embodiments, the health report may be color-coded to represent various ranges of operating conditions, such as ideal/good condition (green), concerning/fair condition (yellow), and poor/critical condition (red), or any suitable operating condition levels and colors. The health report may be presented at a display 400 of a display system 134, presented at a display 400 of an external system 200, and/or may be stored at archive 138 or any suitable data storage medium.

Figure 4:
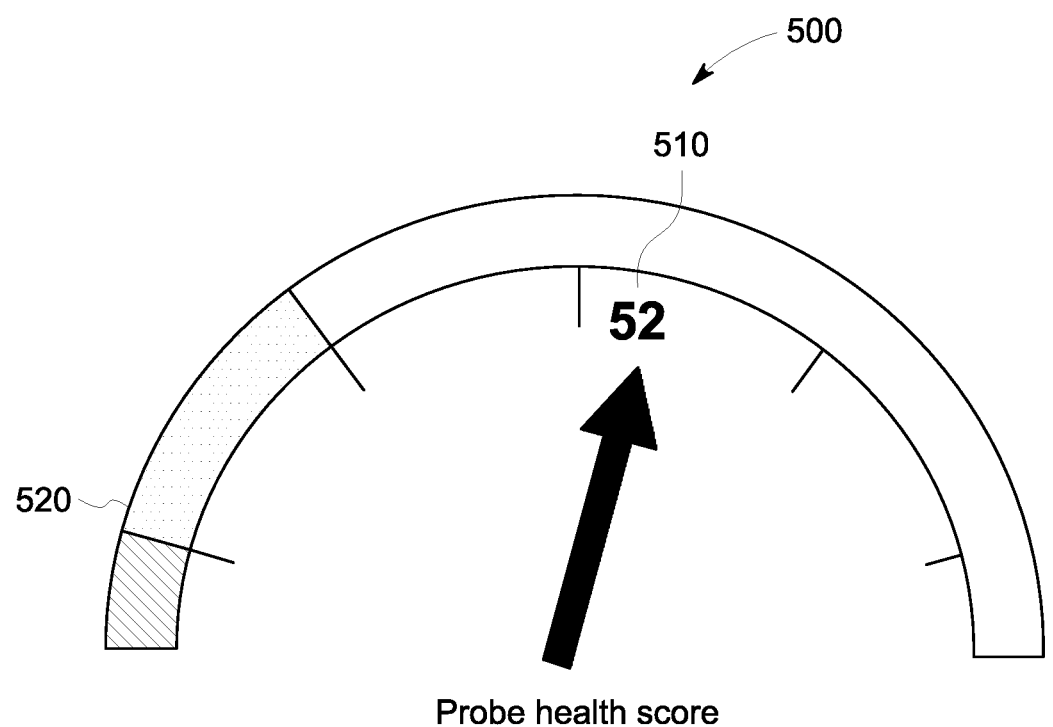
FIG. 4 is an exemplary display of a health report providing a global score for an overall health of an ultrasound probe, in accordance with various embodiments.
Figure 4:
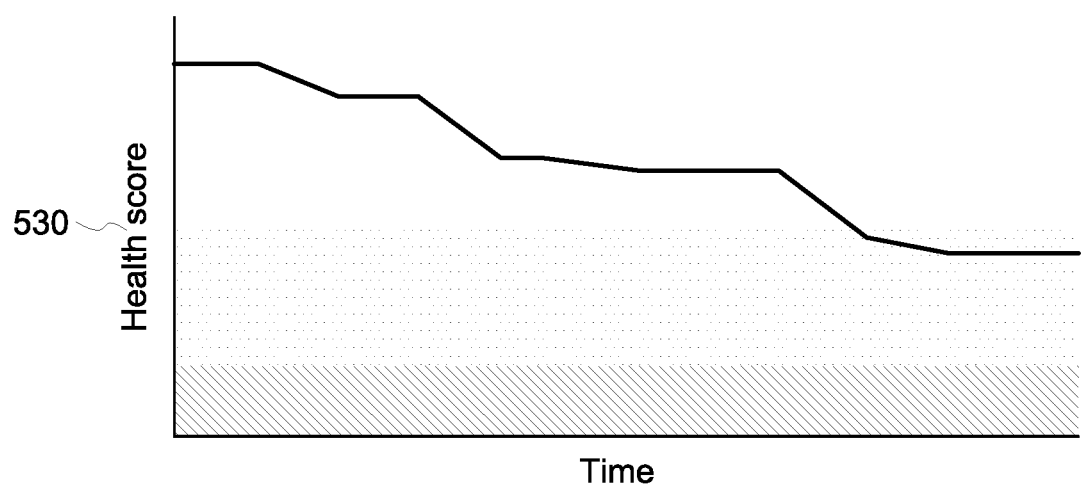

Referring again to FIG. 1, the health report may provide a global score, generated by the health analysis processor 140, for an ultrasound probe 104. The global score may be determined by the health analysis processor 140 based in part on the individual scores of each of the ultrasound probe components. FIG. 4 is an exemplary display 500 of a health report providing a global score 510, 520, 530 for an overall health of an ultrasound probe 104, in accordance with various embodiments. Referring to FIG. 4, the display 500 presents a health report providing a global score 510, 520, 530 of an ultrasound probe 104. The global score may be presented as a numerical value 510, a visual icon 520, a graphical representation of the global score over time 530, and/or any suitable visual identifier of the global score. The global score 510, 520, 530 may be color-coded to represent various ranges of operating conditions, such as ideal/good condition (green), concerning/fair condition (yellow), and poor/critical condition (red), or any suitable operating condition levels and colors. The health report may be presented at a display 500 of a display system 134, presented at a display 500 of an external system 200, and/or may be stored at archive 138 or any suitable data storage medium.

Referring again to FIG. 1, the health analysis processor 140 comprises suitable logic, circuitry, interfaces and/or code that may be operable to automatically determine and present proposed service actions for an analyzed ultrasound probe 104. For example, the health analysis processor 140 may be configured to determine, for each of the ultrasound probe components, whether a health status of the ultrasound probe component is outside of a target range. The health analysis processor 140 may be configured to determine a proposed service action to address each of the ultrasound probe components outside of the target range. For example, the proposed service action may include repairing, replacing, or the like, the ultrasound probe 104 and/or one or more ultrasound probe components having health scores outside of the target range. The health analysis processor 140 may present the proposed service action(s) for the ultrasound probe 104 and/or each of the ultrasound probe components having health scores outside of the target range at a display device 134 of the ultrasound system 100 or a display device of an external system 200. Additionally and/or alternatively, the proposed service action(s) may be stored at archive 138 and/or at any suitable data storage medium.

Figure 5:
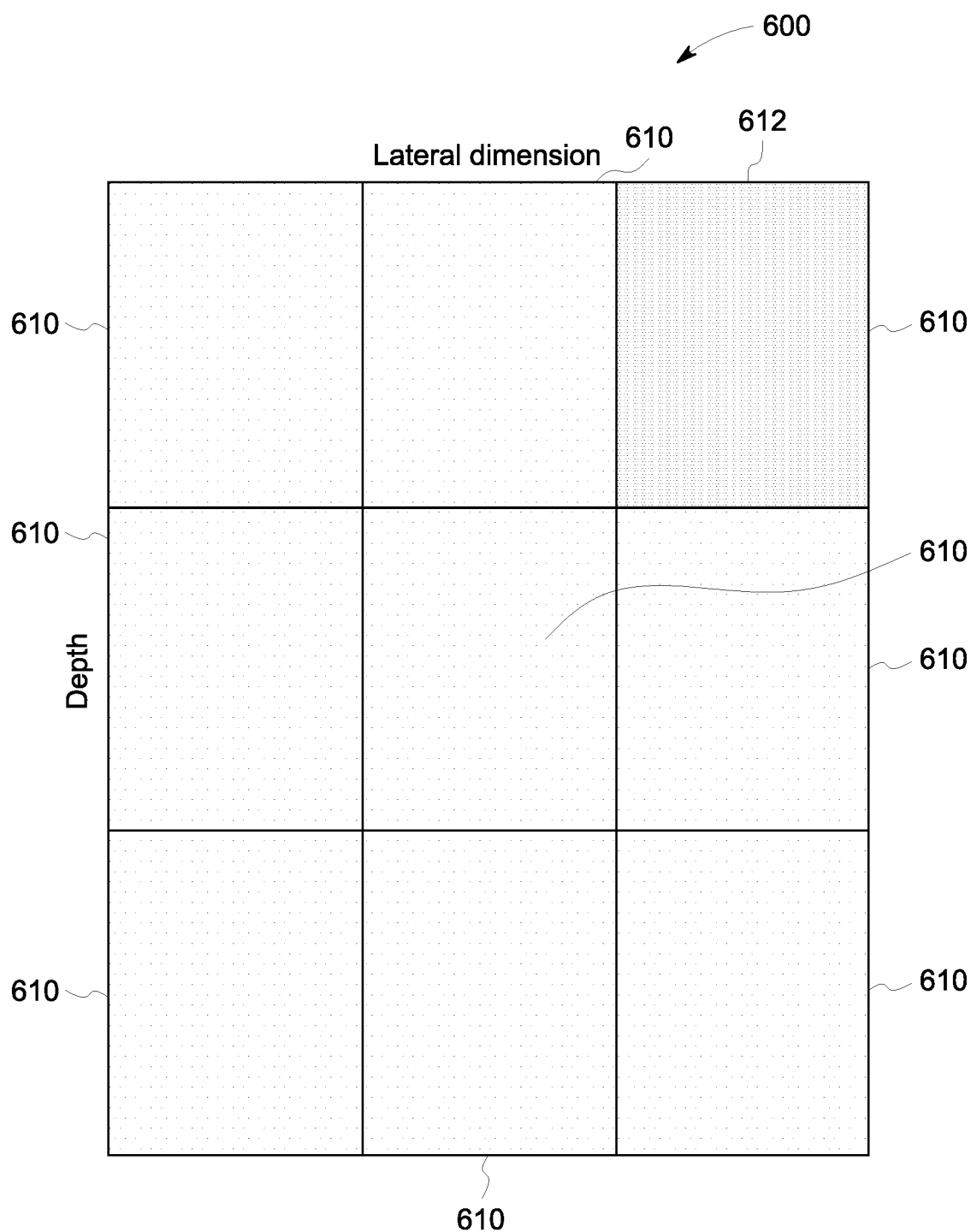
FIG. 5 is an exemplary display of a graphical representation of an imaged area that provides an estimation of image quality, in accordance with various embodiments.

The health analysis processor 140 may comprise suitable logic, circuitry, interfaces and/or code that may be operable to automatically generate and present a graphical representation of an imaged area having labeled zones estimating image quality degradation. For example, the graphical representation may include a plurality of zones. Each of the zones may include a label of an estimation of image quality degradation that would occur in each of the zones based on the determined health status for each of the ultrasound probe components. The labels may be text, numerical labels, color-coded shading, and/or any suitable identifier of an estimated image quality degradation. FIG. 5 is an exemplary display 600 of a graphical representation of an imaged area that provides an estimation of image quality, in accordance with various embodiments. Referring to FIG. 5, the display 600 presents a graphical representation of an imaged area having a plurality of image zones 610. Each of the zones 610 are labeled by color-coded shading with the top, right zone 610 of the image area including shading 612 corresponding with an estimated image quality degradation greater than the other image area zones 610. The graphical representation may be presented at a display 600 of a display system 134, presented at a display 600 of an external system 200, and/or may be stored at archive 138 or any suitable data storage medium.

Referring again to FIG. 1, the health analysis processor 140 may comprise suitable logic, circuitry, interfaces and/or code that may be operable to automatically generate and present a simulated image based on a numerical phantom using the determined health status for each of the ultrasound probe components. The health analysis processor 140 may be further configured to automatically generate and present a reference image based on the numerical phantom using a new health status for each of the ultrasound probe components. The new health status may correspond with the baseline associated with each of the ultrasound probe components such that the reference image provides a reference for how an image would appear if the ultrasound probe components were operating at the new health status. The health analysis processor 140 may be configured to simultaneously present the simulated image and the reference image at the display system 134 of the ultrasound system 100 or a display system of the external system 200 such that an ultrasound operator or other user may view the amount of image degradation provided by the ultrasound probe 104. The simulated image and/or reference image may be stored at archive 138 or any suitable data storage medium.

The health analysis processor 140 may be configured to export the health report to an external system 200. For example, an external system 200, such as a remote workstation, server, and/or any suitable computing device may be communicatively coupled to the ultrasound system 100. The external system 200 may receive health reports from the ultrasound system 100 and health reports related to additional ultrasound probes 104 from the ultrasound system 100 or other ultrasound systems. The external system 200 may comprise suitable logic, circuitry, interfaces and/or code that may be operable to analyze the health report for the ultrasound probe 104 along with additional health reports obtained for additional ultrasound probes. The external system 200 may be configured to generate a report identifying any problems based on the health report for the ultrasound probe 104 and the health reports of the additional ultrasound probes. The external system 200 may aggregate data over time and/or multiple ultrasound probe 104 units to make some statistical analysis, pattern detection, and/or build predictive models using artificial intelligence algorithms.

The display system 134 may be any device capable of communicating visual information and/or audio information to a user. For example, a display system 134 may include a liquid crystal display, a light emitting diode display, and/or any suitable display or displays. The display system 134 may include speakers configured to provide audio feedback. The display system 134 can be operable to display information and/or provide audio feedback from the signal processor 132 and/or archive 138, such as health reports, service actions, image quality estimates, graphical representations of an imaged area, simulated images based on numerical phantoms, reference images based on numerical phantoms using new health statuses, dynamic image equalization, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), an enterprise archive (EA), a vendor-neutral archive (VNA), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things. In various embodiments, the archive 138 stores health reports, service actions, image quality estimates, graphical representations of an imaged area, simulated images based on numerical phantoms, reference images based on numerical phantoms using new health statuses, baselines, new health statuses, cross-talk acquisition sequence ultrasound images, instructions for monitoring ultrasound probe health, instructions for generating health reports, instructions for providing image quality estimates, and/or instructions for exporting health reports, among other things.

Figure 6:
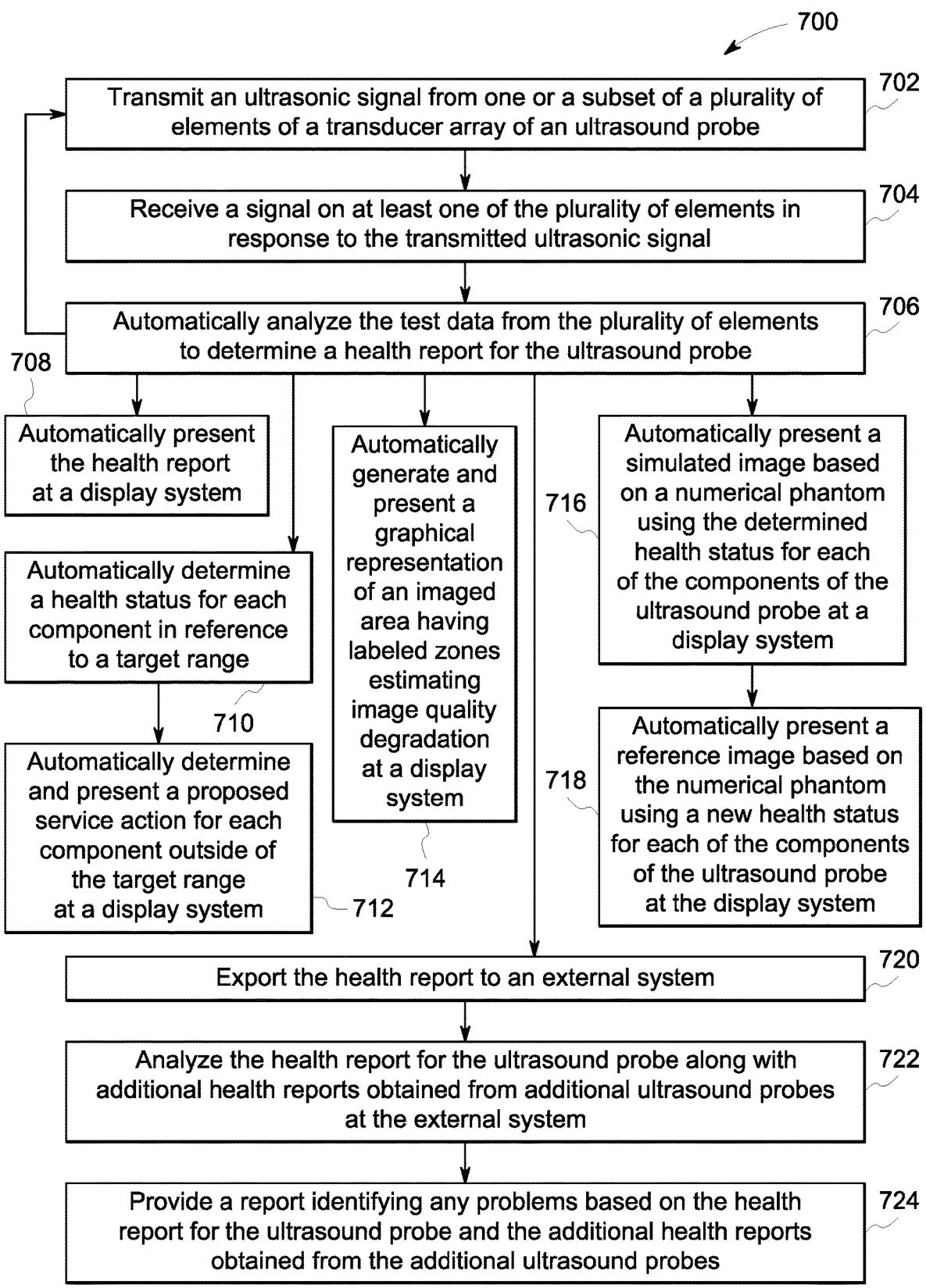
FIG. 6 is a flow chart illustrating exemplary steps that may be utilized for monitoring ultrasound probe health, in accordance with exemplary embodiments.

FIG. 6 is a flow chart 700 illustrating exemplary steps 702-724 that may be utilized for monitoring ultrasound probe health, in accordance with exemplary embodiments. Referring to FIG. 6, there is shown a flow chart 700 comprising exemplary steps 702 through 724. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 702, an ultrasound probe 104 of an ultrasound system 100 may transmit an ultrasonic signal from one (or a subset) of a plurality of elements 106 of a transducer array. For example, the ultrasound probe 104 may initiate acquisition of test data in a scan mode each time the ultrasound probe is connected or used.

At step 704, the ultrasound probe 104 of the ultrasound system 100 may receive a signal on at least one of the plurality of elements 108 in response to the transmitted ultrasonic signal. For example, the signal received by the one or more elements 108 may be received on a receive aperture that is larger than the transmit aperture. The received signal is in response to the ultrasonic signal transmitted at step 702 and is provided to a health analysis processor 140 of a signal processor 132 of the ultrasound system 100 as test data.

At step 706, the signal processor 132 of the ultrasound system 100 automatically analyzes the test data from the plurality of elements to determine a health report for the ultrasound probe 104. Steps 702 through 706 may be repeated to acquire and analyze test data corresponding to signals received in response to the transmission of ultrasonic signals from each of the plurality of elements of the transducer array of the ultrasound probe 104. The health report may be substantially independent of the presence or absence of coupling gel and/or other debris on the ultrasound probe 104. The health analysis processor 140 may analyze test data in the cross-talk zone 302 of the cross-talk acquisition sequence to identify issues with electrical circuits and/or the stack structure of the ultrasound probe 104. The health analysis processor 140 may analyze test data in the lens echoes zone 304 of the cross-talk acquisition sequence to identify issues with the lens, transmit transducer elements 106, and/or receive transducer elements 108. The health analysis processor 140 may analyze test data in the back-scattering zone 306 of the cross-talk acquisition sequence, for example, to identify issues with the transmit transducer elements 106 and/or receive transducer elements 108. The results of the analysis of the cross-talk acquisition sequence may be used by the health analysis processor 140 to generate a health report. The health report may provide information on the health status of each of the components of the ultrasound probe 104, information of the image quality produced by the ultrasound probe 104, and/or a global score for an overall health of the ultrasound probe 104.

At step 708, the signal processor 132 of the ultrasound system 100 may automatically present the health report at a display system 134. For example, the health analysis processor 140 of the signal processor 132 may present the health report generated at step 706 at a display system 134 of the ultrasound system 100. The health report may provide an individual score 416, 426, 436 for each of the ultrasound probe components 414, 424, 434, such as the cap, lens, matching layer(s), piezoelectric element(s), CMUT element(s), MUT element(s), backing structure, flex, wire, ASIC, and/or oil, as shown in FIG. 3, for example. The individual scores 416, 426, 436 may be in reference to a baseline 412, 422, 432. The health report may be represented as bar charts, lists, graphs, numerical scores, or any suitable visual identifier of the component 410, 420, 430 and element 414, 424, 434 scores 416, 426, 436. In various embodiments, the health report may be color-coded to represent various ranges of operating conditions, such as ideal/good condition (green), concerning/fair condition (yellow), and poor/critical condition (red), or any suitable operating condition levels and colors. Additionally and/or alternatively, the health report may provide a global score 510, 520, 530 for the ultrasound probe 104, as shown in FIG. 4, for example. The global score 510, 520, 530 may be determined by the health analysis processor 140 based in part on the individual scores of each of the ultrasound probe components. The global score may be presented as a numerical value 510, a visual icon 520, a graphical representation of the global score over time 530, and/or any suitable visual identifier of the global score. The global score 510, 520, 530 may be color-coded to represent various ranges of operating conditions, such as ideal/good condition (green), concerning/fair condition (yellow), and poor/critical condition (red), or any suitable operating condition levels and colors.

At step 710, the signal processor 132 of the ultrasound system 100 may automatically determine a health status for each component in reference to a target range. For example, the health analysis processor 140 of the signal processor 132 may be configured to determine, for each of the ultrasound probe components, whether a health status of the ultrasound probe component is outside of a target range. The target range may correspond with a range of acceptable health scores for a particular component of the ultrasound probe 104.

At step 712, the signal processor 132 of the ultrasound system 100 may automatically determine and present a proposed service action for each component outside of the target range at a display system 134. For example, the health analysis processor 140 of the signal processor 132 may be configured to determine a proposed service action to address each of the ultrasound probe components outside of the target range. The proposed service action may include repairing, replacing, or the like, the one or more ultrasound probe components having health scores outside of the target range. The health analysis processor 140 may present the proposed service action(s) for each of the ultrasound probe components having health scores outside of the target range at a display device 134 of the ultrasound system 100.

At step 714, the signal processor 132 of the ultrasound system 100 may automatically generate and present a graphical representation of an imaged area having labeled zones estimating image quality degradation at the display system 134. For example, the graphical representation may include a plurality of zones 610 as shown in FIG. 5, for example. Each of the zones 610 may include a label of an estimation of image quality degradation that would occur in each of the zones based on the determined health status for each of the ultrasound probe components. The labels may be text, numerical labels, color-coded shading, and/or any suitable identifier of an estimated image quality degradation. The graphical representation may be presented at a display 600 of a display system 134 of the ultrasound system 100.

At step 716, the signal processor 132 of the ultrasound system 100 may automatically present a simulated image based on a numerical phantom using the determined health status for each of the components of the ultrasound probe 104 at a display system 134. For example, the health analysis processor 140 of the signal processor 132 may generate the simulated and present the simulated image at the display system 134 to demonstrate a current estimated image quality provided by the ultrasound probe 104.

At step 718, the signal processor 132 of the ultrasound system 100 may automatically present a reference image based on the numerical phantom using a new health status for each of the components of the ultrasound probe 104 at the display system 134. For example, the health analysis processor 140 of the signal processor 132 may be configured to automatically generate and present a reference image based on the numerical phantom using a new health status for each of the ultrasound probe components. The new health status may correspond with the baseline associated with each of the ultrasound probe components such that the reference image provides a reference for how an image would appear if the ultrasound probe components were operating at the new health status. The health analysis processor 140 may be configured to simultaneously present the simulated image of step 716 and the reference image of step 718 at the display system 134 of the ultrasound system 100 such that a user may visualize any image degradation provided by the ultrasound probe 104 having the current health status with reference the reference image provided based on the new health status. In various embodiments, the health analysis processor 140 may automatically indicate one or more regions on the simulated image that show a degradation in image quality compared to the reference image.

At step 720, the signal processor 132 of the ultrasound system may export the health report to an external system 200. For example, an external system 200, such as a remote workstation, server, and/or any suitable computing device may be communicatively coupled to the ultrasound system 100. The external system 200 may receive health reports from the ultrasound system 100 and health reports related to additional ultrasound probes 104 from the ultrasound system 100 or other ultrasound systems.

At step 722, the external system 200 may analyze the health report for the ultrasound probe 104 along with additional health reports obtained from additional ultrasound probes. For example, the external system 200 may analyze the health reports of the ultrasound probes to determine problems with the ultrasound probes.

At step 724, the external system 200 may provide a report identifying any problems based on the health report for the ultrasound probe 104 and the additional health reports obtained from the additional ultrasound probes.

Aspects of the present disclosure monitor ultrasound probe health for an ultrasound probe 104 having a transducer array comprising a plurality of elements 106, 108. In accordance with various embodiments, the method 700 may comprise acquiring test data from the plurality of elements 106, 108 by, for each of the plurality of elements 106, 108, by transmitting 702 an ultrasonic signal from one or a subset of the plurality of elements 106, and receiving 704 a signal on at least one of the plurality of elements 108 based on the transmitted ultrasonic signal. The method 700 may comprise automatically analyzing 706 the test data from the plurality of elements 106, 108 to determine a health report for the ultrasound probe 104. The health report may include a health status for each of a plurality of components 410, 420, 430 of the ultrasound probe 104. At least one 430 of the plurality of components 410, 420, 430 may not be part of a transducer array. The method 700 may comprise automatically displaying 708 the health report on a display device 134. The health report may include information 416, 426, 436 for at least one of the plurality of components 410, 420, 430.

In a representative embodiment, the health report comprises a global score 510, 520, 530 for the ultrasound probe 104. In an exemplary embodiment, the health report comprises an individual score 416, 426, 436 for each of the plurality of components 410, 420, 430. In various embodiments, the method 700 comprises determining 710 that the health status for one of the plurality of components 410, 420, 430 is outside of a target range. The method 700 may comprise determining 712 a proposed service action to address the one of the plurality of components 410, 420, 430 with the health status that is outside of the target range. The method 700 may comprise displaying 712 the proposed service action on the display device 134. In certain embodiments, the plurality of components 410, 420, 430 includes at least one of a cap, a lens 430, 434, a matching layer, a piezoelectric element 410, 414, 420, 424, a CMUT element, a MUT element, a backing structure, a flex, a wire, an ASIC, or an amount of oil. In a representative embodiment, the method 700 comprises automatically generating and displaying 714 on the display device 134 an estimation of image quality. In an exemplary embodiment, the estimation of image quality comprises a graphical representation of an imaged area 600. The graphical representation of the imaged area 600 may comprise a plurality of zones 610. Each of the plurality of zones may be color-coded 612 based on an estimate of image quality degradation that would occur in each of the plurality of zones 610 based on the determined health status for each of the plurality of components 410, 420, 430. In various embodiments, the estimation of image quality comprises generating and displaying 716 on the display device 134 a simulated image based on a numerical phantom using the determined health status for each of the plurality of components 410, 420, 430 of the ultrasound probe 104. In a representative embodiment, the method 700 comprises generating and displaying 718 a reference image on the display device 134 based on the numerical phantom using a new health status for each of the plurality of components 410, 420, 430 of the ultrasound probe 104.

In certain embodiments, the method 700 comprises exporting 720 the health report for the ultrasound probe 104 to a remote location 200. The method 700 may comprise analyzing 722 the health report for the ultrasound probe 104 along with a plurality of additional health reports obtained from additional ultrasound probes at the remote location 200. The method 700 may comprise providing 724 a report identifying any problems based on the health report for the ultrasound probe 104 and the plurality of additional health reports obtained from the additional ultrasound probes. In an exemplary embodiment, the at least two or more of the plurality of elements 108 are adjacent either to each other or the one of the plurality of elements 106. In certain embodiments, the health report may include information 416, 426, 436 for at least one of the plurality of components 410, 420, 430 that is negatively impacting image quality due to a degradation compared to a baseline 412, 422, 432. In various embodiments, the baseline 412, 422, 432 comprises a new health status for each of the plurality of components 410, 420, 430 of the ultrasound probe 104. In certain embodiments, the health report is substantially independent of the presence or absence of coupling gel and/or other debris on the ultrasound probe 104. In a representative embodiment, the automatically analyzing 706 the test data from the plurality of elements 106, 108 to determine a health report for the ultrasound probe 104 comprises analyzing cross-talk 302 between the plurality of elements 106, 108.

Various embodiments monitor ultrasound probe health for an ultrasound probe 104 having a transducer array comprising a plurality of elements 106, 108. In accordance with various embodiments, the method 700 may comprise acquiring test data from the plurality of elements 106, 108, for each of the plurality of elements 106, 108, by transmitting 702 an ultrasonic signal from one or a subset of the plurality of elements 106, and receiving 704 a signal on at least one of the plurality of elements 108 based on the transmitted ultrasonic signal. The method 700 may comprise automatically analyzing 706 the test data to determine a health report for the ultrasound probe 104. The health report may include a health status for each of a plurality of components 410, 420, 430 of the ultrasound probe 104. At least one 430 of the plurality of components 410, 420, 430 may not be part of a transducer array. The method 700 may comprise displaying 716, on a display device 134, a simulated image based on a numerical phantom using the determined health status for each of the plurality of components 410, 420, 430 of the ultrasound probe 104. The method 700 may comprise displaying 718, on the display device 134 at the same time as the simulated image, a reference image based on the numerical phantom using a new health status for each of the plurality of components 410, 420, 430 of the ultrasound probe 104.

In an exemplary embodiment, the at least one component 410, 420, 430 comprises the transducer array 410, 420. In various embodiments, the automatically analyzing 706 the test data to determine the health report comprises determining the health status for two or more of a lens 430, 434, a matching layer, a piezoelectric element 410, 414, 420, 424, a CMUT element, a MUT element, a backing structure, a flex, a wire, an ASIC, or an amount of oil. In certain embodiments, the method 700 comprises automatically indicating 718 one or more regions on the simulated image that show a degradation in image quality compared to the reference image. In a representative embodiment, the method 700 comprises displaying 714 a graphical representation of an imaged area 600. The graphical representation of the imaged area 600 may comprise a plurality of zones 610. Each of the plurality of zones 610 may be color-coded 612 based on an estimate of image quality degradation that would occur in each of the plurality of zones 610 based on the health report for the ultrasound probe 104.

Certain embodiments provide an ultrasound system 100 configured to monitor ultrasound probe health for an ultrasound probe 104 having a transducer array having a plurality of elements 106, 108. The ultrasound system 100 may comprise an ultrasound probe 104, a display device 134, and a processor 132, 140. The ultrasound probe 104 may include a transducer array comprising a plurality of elements 106, 108. The processor 132, 140 may be in electronic communication with the ultrasound probe 104 and the display device 134. The processor 132, 140 may be configured to control the ultrasound probe 104 to acquire test data from the plurality of elements 106, 108 by performing steps for each of the plurality of elements 106, 108. The steps may include transmitting a signal from one or a subset of the plurality of elements 106. The steps may include receiving a signal on at least one of the plurality of elements 108 based on the transmitted signal. The processor 132, 140 may be configured to automatically analyze the test data to determine a health report for the ultrasound probe 104. The health report may include a health status for each of a plurality of components 410, 420, 430 of the ultrasound probe 104. At least one 430 of the plurality of components 410, 420, 430 may not be part of the transducer array. The processor 132, 140 may be configured to automatically display, on the display device 134, the health report comprising a health status for each of the plurality of components 410, 420, 430 of the ultrasound probe 104. The health report may include information 416, 426, 436 for at least one of the plurality of components 410, 414, 420, 424, 430, 434.

In various embodiments, the health report comprises an individual score 416, 426, 436 for each of the plurality of components 410, 414, 420, 424, 430, 434. In a representative embodiment, the processor 132, 140 may be configured to automatically analyze the test data to determine a health report for the ultrasound probe 104 when there is gel on the ultrasound probe 104. In an exemplary embodiment, the processor 132, 140 may be further configured to generate and display on the display device 134 a simulated image based on a numerical phantom using the determined health status for each of the plurality of components 410, 420, 430 of the ultrasound probe 104. In certain embodiments, the health report may include information 416, 426, 436 for at least one of the plurality of components 410, 420, 430 that is negatively impacting image quality due to a degradation compared to a baseline 412, 422, 432.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for monitoring ultrasound probe health for an ultrasound probe having a transducer array having a plurality of elements.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for monitoring ultrasound probe health for an ultrasound probe having a transducer array comprising a plurality of elements, the method comprising:
   acquiring test data from the plurality of elements by performing the following steps for each of the plurality of elements:
      transmitting an ultrasonic signal from one or a subset of the plurality of elements;
      receiving a signal on at least one of the plurality of elements based on the transmitted ultrasonic signal;
   automatically analyzing the test data from the plurality of elements to determine a health report for the ultrasound probe, wherein the health report includes a health status for each of a plurality of components of the ultrasound probe, wherein at least one of the plurality of components is not part of the transducer array; and
   automatically displaying the health report on a display device, wherein the health report includes information for at least one of the plurality of components.

2. The method of claim 1, wherein the health report comprises a global score for the ultrasound probe.

3. The method of claim 1, wherein the health report comprises an individual score for each of the plurality of components.

4. The method of claim 1, further comprising:
   determining that the health status for one of the plurality of components is outside of a target range;
   determining a proposed service action to address the one of the plurality of components with the health status that is outside of the target range; and
   displaying the proposed service action on the display device.

5. The method of claim 1, wherein the plurality of components includes at least one of a cap, a lens, a matching layer, a piezoelectric element, a capacitive micro-machined ultrasonic transducer (CMUT) element, a micro-machined ultrasonic transducers (MUT) element, a backing structure, a flex, a wire, an application-specific integrated circuit (ASIC), or an amount of oil.

6. The method of claim 1, further comprising automatically generating and displaying on the display device an estimation of image quality.

7. The method of claim 6, wherein the estimation of image quality comprises a graphical representation of an imaged area, wherein the graphical representation of the imaged area comprises a plurality of zones, wherein each of the plurality of zones is color-coded based on an estimate of image quality degradation that would occur in each of the plurality of zones based on the determined health status for each of the plurality of components.

8. The method of claim 7, wherein the estimation of image quality comprises generating and displaying on the display device a simulated image based on a numerical phantom using the determined health status for each of the plurality of components of the ultrasound probe.

9. The method of claim 8, further comprising generating and displaying a reference image on the display device based on the numerical phantom using a new health status for each of the plurality of components of the ultrasound probe.

10. The method of claim 1, further comprising:
exporting the health report for the ultrasound probe to a remote location;
analyzing the health report for the ultrasound probe along with a plurality of additional health reports obtained from additional ultrasound probes at the remote location; and
providing a report identifying any problems based on the health report for the ultrasound probe and the plurality of additional health reports obtained from the additional ultrasound probes.

11. The method of claim 1, wherein the at least two or more of the plurality of elements are adjacent either to each other or the one of the plurality of elements.

12. The method of claim 1, wherein the health report includes information for at least one of the plurality of components that is negatively impacting image quality due to a degradation compared to a baseline.

13. The method of claim 12, wherein the baseline comprises a new health status for each of the plurality of components of the ultrasound probe.

14. The method of claim 1, wherein the health report is substantially independent of the presence or absence of coupling gel and/or other debris on the ultrasound probe.

15. The method of claim 1, wherein said automatically analyzing the test data from the plurality of elements to determine a health report for the ultrasound probe comprises analyzing cross-talk between the plurality of elements.

16. A method for monitoring ultrasound probe health for an ultrasound probe having a transducer array comprising a plurality of elements, the method comprising:
acquiring test data from the plurality of elements by performing the following steps for each of the plurality of elements:
transmitting an ultrasonic signal from one or a subset of the plurality of elements;
receiving a signal on at least one of the plurality of elements based on the transmitted ultrasonic signal;
automatically analyzing the test data to determine a health report for the ultrasound probe, wherein the health report includes a health status for each of a plurality of components of the ultrasound probe, wherein at least one of the plurality of components is not part of the transducer array;
displaying, on a display device, a simulated image based on a numerical phantom using the determined health status for each of the plurality of components of the ultrasound probe; and
displaying, on the display device at the same time as the simulated image, a reference image based on the numerical phantom using a new health status for each of the plurality of components of the ultrasound probe.

17. The method of claim 16, wherein the at least one component comprises the transducer array.

18. The method of claim 16, wherein said automatically analyzing the test data to determine the health report comprises determining the health status for two or more of a lens, a matching layer, a piezoelectric element, a CMUT element, a MUT element, a backing structure, a flex, a wire, an ASIC, or an amount of oil.

19. The method of claim 16, further comprising automatically indicating one or more regions on the simulated image that show a degradation in image quality compared to the reference image.

20. The method of claim 16, further comprising displaying a graphical representation of an imaged area, wherein the graphical representation of the imaged area comprises a plurality of zones, wherein each of the plurality of zones is color-coded based on an estimate of image quality degradation that would occur in each of the plurality of zones based on the health report for the ultrasound probe.

21. An ultrasound system, comprising:
an ultrasound probe including a transducer array comprising a plurality of elements;
a display device;
a processor in electronic communication with the ultrasound probe and the display device, wherein the processor is configured to:
control the ultrasound probe to acquire test data from the plurality of elements by performing the following steps for each of the plurality of elements:
transmit a signal from one or a subset of the plurality of elements;
receive a signal on at least one of the plurality of elements based on the transmitted signal;
automatically analyze the test data to determine a health report for the ultrasound probe, wherein the health report includes a health status for each of a plurality of components of the ultrasound probe, wherein at least one of the plurality of components is not part of the transducer array;
automatically display, on the display device, the health report comprising a health status for each of the plurality of components of the ultrasound probe, wherein the health report includes information for at least one of the plurality of components.

22. The ultrasound system of claim 21, wherein the health report comprises an individual score for each of the plurality of components.

23. The ultrasound system of claim 21, wherein processor is configured to automatically analyze the test data to determine a health report for the ultrasound probe when there is gel on the ultrasound probe.

24. The ultrasound system of claim 21, wherein the processor is further configured to generate and display on the display device a simulated image based on a numerical phantom using the determined health status for each of the plurality of components of the ultrasound probe.

25. The ultrasound system of claim 21, wherein the health report includes information for at least one of the plurality of components that is negatively impacting image quality due to degradation compared to a baseline.

* * * * *